(12) United States Patent
Makesh

(10) Patent No.: US 11,628,309 B2
(45) Date of Patent: *Apr. 18, 2023

(54) SYSTEM AND METHOD FOR TREATING PATIENTS IN A CONTROLLED SETTING

(71) Applicant: Orcus Systems and Solutions, Inc., Madison, OH (US)

(72) Inventor: Nesian Jean Makesh, Auburn Township, OH (US)

(73) Assignee: Orcus Systems and Solutions, Inc., Madison, OH (US)

( * ) Notice: Subject to any disclaimer, the term of this patent is extended or adjusted under 35 U.S.C. 154(b) by 993 days.

This patent is subject to a terminal disclaimer.

(21) Appl. No.: 16/153,785

(22) Filed: Oct. 7, 2018

(65) Prior Publication Data

US 2019/0038911 A1 Feb. 7, 2019

Related U.S. Application Data

(63) Continuation of application No. 14/210,916, filed on Mar. 14, 2014, now Pat. No. 10,092,772.

(60) Provisional application No. 61/952,395, filed on Mar. 13, 2014, provisional application No. 61/789,714, filed on Mar. 15, 2013.

(51) Int. Cl.
*A61N 5/06* (2006.01)
*A61M 21/00* (2006.01)
*A61B 5/00* (2006.01)

(52) U.S. Cl.
CPC ......... *A61N 5/062* (2013.01); *A61M 21/0094* (2013.01); *A61N 5/0618* (2013.01); *A61B 5/00* (2013.01); *A61M 2021/0005* (2013.01); *A61M 2021/0027* (2013.01); *A61M 2021/0044* (2013.01); *A61M 2021/0066* (2013.01); *A61M 2205/3368* (2013.01); *A61M 2205/3561* (2013.01); *A61M 2205/3584* (2013.01); *A61M 2205/502* (2013.01); *A61M 2205/52* (2013.01)

(58) Field of Classification Search
CPC ...... A61M 21/0094; A61M 2021/0005; A61M 2021/0016; A61M 2021/0027; A61M 2021/0044; A61N 5/0618; A61N 5/062; A61G 10/00
See application file for complete search history.

(56) References Cited

U.S. PATENT DOCUMENTS 6,527,700 B1 3/2003 Manico
10,092,772 B1 * 10/2018 Makesh ............ A61M 21/0094
(Continued)

*Primary Examiner* — William H Matthews
(74) *Attorney, Agent, or Firm* — Bodi Law LLC

(57) ABSTRACT

A system and methodology for treating patients with dementia using a methodology which includes a functional assessment of the patient to determine the patient's cognitive and daily living capabilities that is used to prepare a functional assessment of the patient to determine the patient's cognitive and daily living capabilities. The treatment uses a plurality of rooms providing living quarters the patients, with a control system executing a lighting program for a lighting system that is configured to simulate a plurality of different phases of daylight over a period of time. Furthermore, the lighting system includes a structure for adapted for simulating clouds. Also, the system provides at least one room having the lighting system and providing plants and flowing water providing an illusion of the room being outdoors.

24 Claims, 12 Drawing Sheets

(56) References Cited

U.S. PATENT DOCUMENTS

2008/0103561 A1     5/2008   Moscovici
2010/0023094 A1     1/2010   Smith

\* cited by examiner

SYSTEM AND METHOD FOR TREATING PATIENTS IN A CONTROLLED SETTING

CROSS-REFERENCES TO RELATED APPLICATIONS

This application is a continuation of application Ser. No. 14/210,916 filed on Mar. 14, 2014 issuing as U.S. Pat. No. 10,092,772 on Oct. 9, 2018, which claims the benefit of U.S. provisional patent application Ser. No. 61/789,714 filed on Mar. 15, 2013. This application also claims the benefit of U.S. provisional patent application Ser. No. 61/952,395 filed on Mar. 13, 2014. All of these documents are incorporated herein by reference.

BACKGROUND

This application relates generally to system and method of providing a controlled setting for a patient to improve the treatment and lifestyle of the patient, in particular where mental deterioration of the patient is a symptom of a disease, such as in the case of Alzheimer's disease, for example.

Generally, it has been found that patients with mental diseases, such as Alzheimer's disease, have a difficult time adjusting to, and living in, controlled environments that may be necessary for their care and treatment. Desired is a system and method that would ease such a transition and, preferably, slow the mental deterioration and difficulties in coping that accompany such a disease as it progresses.

SUMMARY

Provided are a plurality of example embodiments, including, but not limited to, a method of treating a patient with dementia, comprising the steps of:
  providing a plurality of rooms providing living quarters for at least one patient;
  providing a computer control system for executing a lighting program; and
  providing a lighting system in at least one of the rooms, the lighting system being configured to be the controlled by the computer control system executing the lighting program for generating light from the lighting system adapted to simulate a plurality of different phases of daylight over a period of time.

Also provided is a method of treating a plurality of patients with dementia, comprising the steps of:
  providing a functional assessment of the patients to determine each patient's cognitive and daily living capabilities;
  preparing, for each one of the patients using the functional assessment of each one of the patients, a customized cognitive and daily living capabilities plan that each patient can execute;
  rehearsing individually with each patient on a daily basis the customized cognitive and daily living capabilities plan for that patient;
  providing a plurality of rooms providing living quarters for a plurality of patients, wherein at least some of the rooms are arranged in a manner to remind the patients of living styles that were utilized during the patients' childhood;
  providing a lighting system in a plurality of the rooms, the lighting system being configured to generate light adapted to simulate a plurality of different phases of daylight over a period of time; and
  providing at least one room comprising the lighting system, wherein the room further includes providing plants and flowing water providing an illusion of the room being outdoors.

Further provided are any of the above methods, wherein the functional assessment is performed over a period of days.

Further provided are any of the above methods, wherein the customized cognitive and daily living capabilities plan includes a plan for dressing the patient and for personal grooming of the patient, such that the patient performs as many functions of the plan as the functional assessment of the patient has determined are possible.

Further provided are any of the above methods, wherein the assessment determines an assessment of a plurality of learning areas of the patient including: social-emotional skill, large motor skill, small motor skill, visual skill, reasoning skill, language skill and listening skill for use in implementing the plan.

Further provided are any of the above methods, wherein the plan is updated to include new learned activities of the patient as the patent progresses through the treatment.

Also provide is a system configured for providing any of the above methods.

Further provide is a system for treating a patient with dementia, comprising: a plurality of rooms providing living quarters for at least one patient; a computer control system for executing a lighting program; a lighting system in at least one of the rooms, the lighting system being configured to be the controlled by the computer control system executing the lighting program for generating light from the lighting system adapted to simulate a plurality of different phases of daylight over a period of time, wherein the plurality of different phases of daylight include morning, daytime, evening, and nighttime, and wherein the lighting system includes a structure for adapted for simulating clouds. The system also comprising at least one room comprising the lighting system, wherein the room further includes providing plants and flowing water providing an illusion of the room being outdoors.

Also provided are additional example embodiments, some, but not all of which, are described hereinbelow in more detail.

Figure 1:
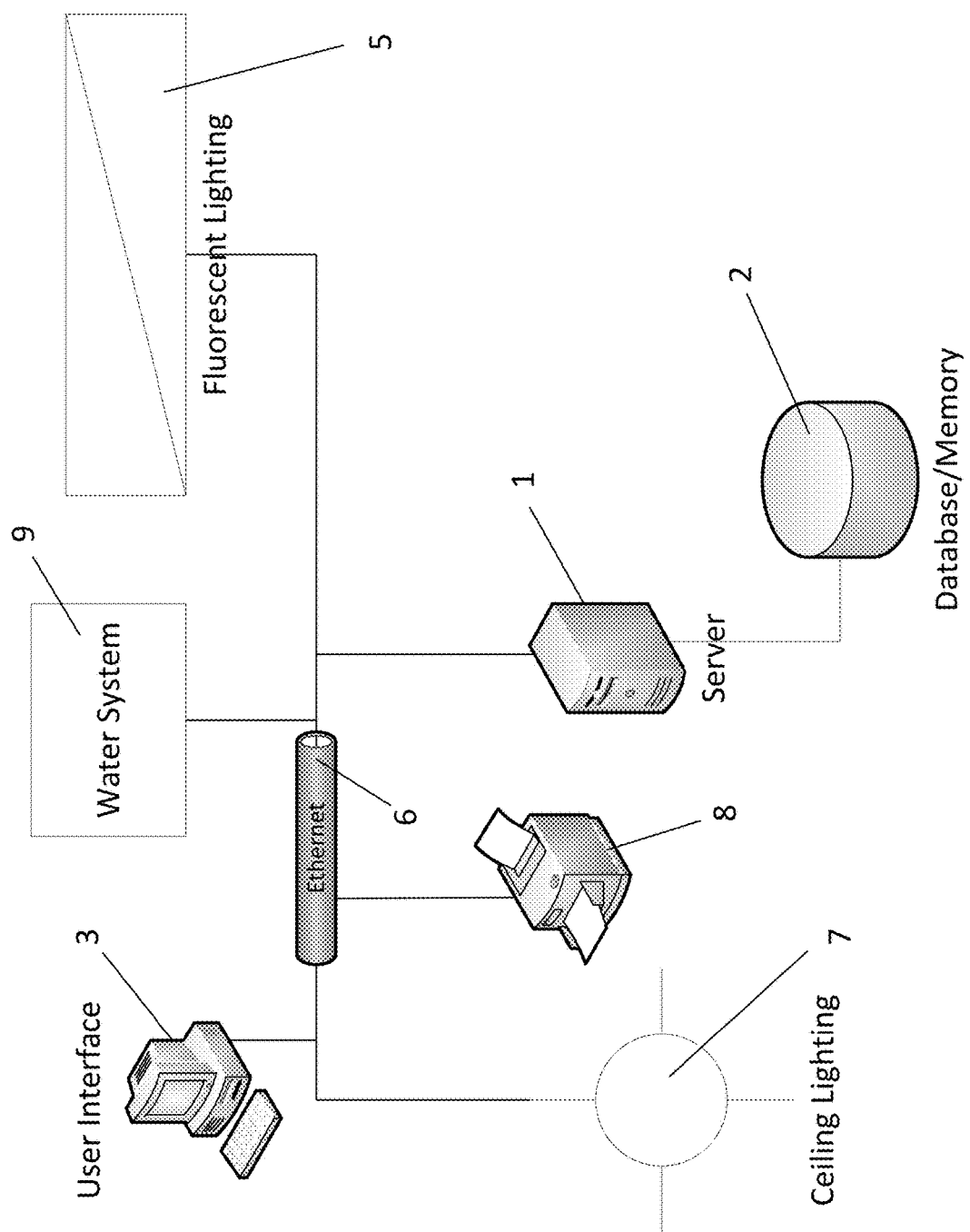
FIG. 1 is a block diagram showing computer hardware for implementing one example embodiment of the system and FIG. 1A is a schematic of a possible room layout for group settings.

The features and advantages of the example embodiments described herein will become apparent to those skilled in the art to which this disclosure relates upon reading the following description, with reference to the accompanying drawings attached hereto.

DETAILED DESCRIPTION OF THE EXAMPLE EMBODIMENTS

Individuals receive stimulus from their surrounding environment. Individual actions and response are based on their perception and perception is based on their past experiences.

Sky ceilings, cascade water falls, gazebos, pergolas, and suites built using materials as homes gives the perception that the individuals with dementia, such as those with Alzheimer's disease, don't live in a lock-down facility. They preferably get the impression that they live in a natural setting. The patients get the impression of living in a subdivision or a housing development, similar to what they have gotten accustomed to over their lifetime. They get to live in a home surrounded by lush landscape and nature (Plants and trees). The sky ceiling gets brighter in the morning, and darker in the evening giving them the impression that they exist in a natural environment with the lighting reflecting the rise and fall of the sun, with the periods of twilight and dusk. Hence, the patients can continue to experience the normal natural setting and routine of life and survival that would be lost in a typical institutional environment.

Living quarters, such as homes, apartments, and/or rooms are designed and built to emulate the time-frame 1920-1940 (the period of the patient prior to full adulthood) helping the patients to associate and come in terms with their residual long term memories. Individuals with Dementia/Alzheimer's disease typically have some of their long term memories intact, and in particular memories of their youth. It is good to provide a familiar environment, an environment that the patient remembers from their past and that is registered in their long-term memory. Such a setting helps them to be at peace and reduces stress and conflict. There is no conflict or inconsistency with their existing memories and they are at terms with their residual long term memory. They are not exposed to any new unfamiliar, threatening environment that is in contrast to their long-term memories. They are not trying to figure out or process new information which would require use of their damaged short-term memories.

Providing such a controlled environment gives patients the impression that they live in a normal natural setting like the way they have lived all their lives. The desire to seek exit and induced stress are dramatically minimized. They feel like they live outdoors and the desire to leave the facility is largely diminished. The risk for elopement could be dramatically decreased. Providing an environment and setting that the clients are familiar with also eliminates unwanted emotions such as anxiety and depression thus promoting a healthy life style. When anxiety and depression are eliminated, there is a good possibility that the individual is relaxed and relaxation helps in alignment of thoughts and memories. When thoughts are aligned, certain memories could return and assist the individual to function and perform activities of daily living at their maximum potential. Humans perform at their highest potential when they are stress free with no anxiety or depression. Memory and thought conflicts can cause a lot of stress and burden, limiting and suppressing the patient's ability to be functional.

Imagine a person getting ready to go to work and looking for the car keys. But the person is unable to find the car keys. The keys are not in the basket or the key holder where they are usually placed. The person is typically very diligent about putting things away in designated places. The night before, the person had done some grocery shopping and had carried grocery bags into his or her home. While arranging the groceries, the person was distracted by a phone call or a spouse asking for something and children wanting something and in the process, the person had placed the car keys somewhere not in the usual place. Now the person is unable to find the keys. The person begins to look at every spot that possibly could have the keys, from the kitchen counter to the bathroom counter. Steps are traced back. The person just cannot remember. Such a person goes through a string of emotions from frustration, irritation, anger, and sometimes even blaming the spouse and kids. The more the person experiences those emotions, the more it becomes hard for that person to remember and trace the steps back.

These emotions become a barrier to accessing the person's short-term memory. However, if the person is calm, composed, less anxious, less irritated and non-emotional, the chances of that person tracing a memory path is a lot better than when clouded by emotions. The person is able to access memories and thoughts much more clearly. Imagine what individuals with dementia/Alzheimer's go through on a daily basis. They are unable to remember events, activities, names, and thoughts from the recent past. They are bound to go through emotions such as frustration, irritation, anger, agitation etc. A controlled environment such as described herein provides them with a regular routine of day and night, thereby eliminating unwanted emotions to help them clearly access their residual memories. Thus enhancing their quality of life. Giving them a dignified life.

Progressive Lowered Stress Threshold:

Humans tend to go through their day subjected to different stimuli from the environment and within their bodies. These stimuli can cause stress. Most humans find a way to unwind themselves at the end of the day. Some listen to their favorite music, retire with a glass of wine after getting home, sit on the porch and listen to the nature sounds, watch the birds, play with their pets, etc. A person could have a great day or a bad day, but no matter what kind of day, a person must unwind, relax, distress. Humans get tired at the end of the day irrespective of the kind of day they have.

Similarly, individuals with Dementia/Alzheimer's disease are subjected to stress. Though they don't work like younger individuals, they do go through similar stress. Stress could be due to memory and thought conflicts. It could be due to being unable to perform a certain ADL (Activity of Daily Living) function. It could be because of pain, discomfort, hunger, thirst etc. Sometimes they are unable to express their desires, needs and wants. Their common mode of expression tends to be through emotions such as frustration, irritation, anger, agitation, aggression etc. They are unable to distress, unwind, relax, rest like those not afflicted with the disease. Hence, it is desirable to create an environment that will help them dissipate stress. The sky ceiling, the water falls, lush landscape, and plants create an environment that is serene, tranquil and helps the patients to relax. It helps them to be calm and free of any unwanted, undesired, inappropriate emotions. Thus allowing them to lead a life filled with quality and dignity.

Person Environment Occupation:

Normally to execute a desired task, ADL function, vocation or occupation, individuals need to be in symmetry or in alignment with the environment. For example, when on vacation in the Bahamas or on the beach, if the individual tries to recall something related to work, he or she sometimes may have a hard time remembering or recalling. The individual is out of context, and is unable to recall a thought or an experience that originated and developed in another environment or a setting. However, upon return back to work or just by merely driving into the parking lot or going through the main double doors, the thoughts/experiences that the individual has been desperately trying to recall or remember often comes back as if by magic. This is because the individual is back in an environment where the thought originated, or where it was rehearsed. Hence, often the person and the environment must align to execute a desired function.

For example, if given a tooth brush when in a ballroom sometime around 2.00 PM, what is the individual to do with it? It may be put it in a pocket or put it away. However, if given a tooth brush in front of a sink around 6.30 am, there is a good chance that the same individual would brush his or her teeth. The environment is very important for an individual to initiate and complete a desired function. The desire to brush has to be there. The desire to brush is dictated by a need, and in most instances for activities of daily living, this is a function that has been done from 3-4 years of age. Activities of daily living such as feeding, dressing, bathing, grooming, oral hygiene, toileting are functions that have been learned, developed, and practiced since 3-4 years of age. Some of the ADL functions matured and were mastered at 8 years of age. Individuals with dementia/Alzheimer's have their long term memory intact, and therefore, the ability to perform their ADL functions should be there. These functions, if not compromised due to physical deficits could be still be performed by the individuals with Dementia/Alzheimer's disease. These functions could eventually fade away if the desire to initiate and complete the ADL functions is lost.

Due to cognitive deficits during the early stages of the disease, the desire to initiate and complete ADL tasks could diminish. Subjecting and exposing an individual to a natural setting like an environment that takes them through a normal routine day and night could enable them to remind themselves a time to rise, complete morning ADL tasks, time to play, time to eat, and time to retire. Day and night routine may enable them to participate and perform their activities of daily living on a daily basis with or without help. Having them live in an environment that reminds them of a natural setting may enable them to be more compliant with their activities of daily living function.

The staff of the living facility are actively engaged with the individuals on a daily basis in an appropriate environment that will enable them to cooperate, participate and be compliant with their activities of daily living. For example, if an individual is aroused in the morning, led to the bathroom, presented with a toothbrush with paste on it in front of a sink and in front of a mirror, that may motivate the individual to initiate and complete brushing with or without verbal/visual cues. If this is repeated daily by the staff and by the individual, it is an ADL function the individual will continue to retain through repetition.

Patients should be offered a wide variety of activities on different skill levels from which the elderly can choose during independent activity time. A separate time must be allocated for the elderly clients to engage in different independent activities to their choosing and liking. A good program should provide ways for the elderly who tend to do only those activities they feel comfortable with to be successful in a variety of learning experiences. There could be other emotions and distractions that could block them to participate and hence their ability to focus is compromised. Their attention spans are like lightning bolts. Give the elderly stimulating material, frequent activity changes, and your enthusiasm. It will turn the lightning bolt into a steady current of concentration.

Imagine that a person is living inside of a video game, where everything is coming at the person at once and every sight, sound and sensation is a distraction. An individual with Dementia and Alzheimer's disease, getting through a typical day is something like that—and it explains a great deal about how they experience the world. Individuals with Dementia and Alzheimer's disease typically have impairment of functions such as concentration, memory, impulse control, processing speed and an inability to follow directions. Currently, caregivers often feel completely drained by their high energy and seeming inability to focus. Combining simple relaxation techniques such as deep breathing with positive visual imagery helps the brain to improve or learn new skills. For instance, research shows that if a person mentally practices their golf swing, the brain actually records the imaginary trials the same as if they were real trials which leads to improvement on the golf course. Crossword puzzles actually improve attention for words and sequencing ability, while picture puzzles—in which an elderly client with stage III, IV, V and VI disease has to look for things that are "wrong" in the picture or look for hard-to-find objects—also improve attention and concentration.

The late years of person's life have a lot to do with development of desirable characteristics during their early years. The activity is organized around the six developmental areas of the profile-Gross motor, fine motor, visual perception, reasoning, receptive language and expressive language. The activities focus on seven learning areas—Large motor skills, Small motor skills, Visual skills, reasoning, listening skills, language skills and social-emotional development. There is one primary purpose in each activity; several skill areas are often touched on when the activity is presented. When Elderly work together in the activity, they are not only triggering and processing a small-motor skill—they are also processing and experiencing: to share (social-emotional skills), to follow directions (listening skills) and to copy a visual pattern (visual skills). Each activity must be viewed in terms of its potential to speed the ignition of a desired developmental or learning area. The activities are designed to stimulate already learnt basic life skills that were the foundation of intellectual and social endeavor. Consequently, the emphasis is on re igniting a broad range of abilities, and not on the rote learning of isolated "practical" skills such as tying shoe laces.

Theory of Retro Genesis:

This theory hypothesizes that individuals with dementia/Alzheimer's disease reverse develop. They revert back to earlier developmental stages of life. Their cognitive function and abilities to perform activities of daily living will be at the age levels ranging from infancy to twenty year old.

The developmental age groups are as follows—

Infant;

12-18 months;

18 months-3 year old;

4-10/12 year old; and

Teenage to 20 year old.

An elderly patient with a developmental age of 12-18 months will not be able to do an activity designed for 18 months-3 yr. old. The activity must be developmental age specific for the elderly to participate, cooperate, tolerate and to initiate, process and complete an activity.

Basic Ability to Function (BATF):

Allen cognitive levels are used to describe an individual's Best ability to function in the form of a progression of abilities. The Allen cognitive levels provide information about the just-right challenge for the person with dementia/Alzheimer's disease by matching the task complexity with the person's cognitive ability. Abilities remain at every stages of the disease. The identified Allen level/stage of Dementia and Alzheimer helps to identify an individual's basic ability to function and facilitates the already existing function:

Clinical stage 1: Normal

Clinical stage 2: Normal aged forgetfulness

Clinical stage 3: Mild cognitive impairment (Developmental age—teenage to 20s)

Clinical stage 4: Mild Alzheimer disease (Developmental age—4-10/12 year old)

Clinical stage 5: Moderate Alzheimer disease (Developmental age—18 months to 3 year old)

Clinical stage 6: Moderately severe Alzheimer disease (Developmental age—12-18 months)

Clinical stage 7: Severe Alzheimer disease (Infant)

It is important to understand an individual's cognitive level and functional capability. With the disease, individuals revert back to early developmental stages. The above classification is merely a starting point to empower the caregiver with information to approach and engage appropriately. The chart should be used to understand the individual's cognitive and functional personality. The chart by no means directs the caregiver to treat the elderly individual like a child. It enables and equips the caregiver with what to expect and what not to expect. One cannot expect a seven year old to do what a fifteen year old can. The chart enables the caregiver to approach the individuals with dementia/Alzheimer disease with realistic and pragmatic expectations.

Though the patients may show cognitive personality and ADL functions capability corresponding to the age group, infancy to 20 years of age, depending on the severity of the disease, they however, have evolved and developed a personality as they matured and aged with time. This is something that the caregivers must be sensitive to as they interact and engage with the individuals. The individuals should be treated and cared for as adults; however, the individuals physical, functional and cognitive ability should be understood and known to provide the best care that the individual deserves.

An individual's cognitive ability and functional capability with clinical stage 7 disease is similar to an infant. An infant cannot feed itself, cannot dress and bathe itself. It is not a good idea to bathe such an individual in a shower. What happens when one bathes an infant in a shower? The infant is unable to tolerate the activity. The infant cries out loud and is uncomfortable and in pain. The infant cannot tolerate the high pressure jet of water from the shower head. Infants senses are hypersensitive and they are unable to tolerate anything with pressure, loud noises, etc. Their threshold of tolerance to touch, pressure and pain is low. Infants don't do well in a bathtub either. They respond well to soft touch, pleasant sound, good aroma. They cooperate and participate with the caregiver only after they trust the caregiver. They have to feel safe and comfortable before they engage with a caregiver. In a similar fashion it is important for a caregiver to develop the trust and confidence from an individual with dementia/Alzheimer's disease.

Upon a client's admission to a treatment program, a functional assessment is completed to determine a client's cognitive and activities of daily living abilities. The assessment thoroughly focuses on what an individual can do and cannot do. The functional assessment is typically administered by a qualified nurse to gain information related to the individual's cognitive and functional status in order to identify the just-right abilities. This will lead to facilitating the client's highest level of function and safety. The goal of the assessment is to identify the "can do" aspects of function, and is critically important in the development of a care plan. Physical, sensory and emotional elements are required to carry and perform an activity of daily living functions. Appendix A, incorporated herein by reference, is an example of such an assessment.

The cognitive and the ADL functions that the individual can execute are rehearsed and repeated every single day. When a function that an individual can perform is repeated and practiced every day, the chance of the individual losing the ability to perform that particular function diminishes. For example, when an individual has the ability to dress the upper body, the caregiver will encourage and motivate the individual to dress the upper body every day without help. This will enable the individual to go through all the steps of upper body dressing every day. Repetition of this task every day will maintain and enhance the upper body dressing function. There is a good possibility that consistent repetitive practice of a lower function may pave path for learning the next higher function such as lower body dressing. Lower body dressing is more complex than the upper body dressing. Lower body requires postural stability, large and fine motor skills and thought processing.

A thorough functional assessment may take 7 days to establish a baseline. The assessment involves the collection and gathering of information from caregivers that care for the individual during different times of the day and night. The information includes an individual's basic cognitive and ADL functions. The assessor looks for consistencies and patterns in the way an individual performs their cognitive and ADL functions. The data is carefully compiled and a treatment plan is established. The treatment plan will be broken down into ability to feed, ability to groom, ability to perform oral hygiene, ability to dress upper body and lower body, ability to bath upper body and lower body, ability to toilet, ability to ambulate, if wheel chair bound ability to transfer in and out of wheel chair, ability to transfer from wheel chair to bed, ability to transfer from wheel chair to toilet and ability to maneuver a wheel chair. The treatment plan will also be driven by the individual's cognitive abilities such as ability to follow simple one or two step instructions and attention span (ability to focus and concentrate). The treatment plan will also include working on physical abilities such as strength, balance, gross motor coordination and fine motor coordination. The treatment plan will also entail essential behavioral elements such as an individual's desire to initiate and complete an ADL function, and motivation to participate and complete an ADL function. The treatment will be individual centered with focus on an individual's cognitive and ADL function specifics.

For example: Helen is an 89 year old with clinical stage 5 moderate Alzheimer's disease. She can feed herself independently, but needs assistance with grooming and oral hygiene. She can dress her upper body occasionally but requires extensive assistance with lower body dressing. Helen is unable to bath on her own and requires assistance. Helen is independent with ambulation, she likes to walk a lot. The care plan for Helen will be as follows:

Feeding: After a thorough assessment, it was determined that although Helen was independent with feeding self, the following were observed and validated by the caregivers:
1. Helen likes to eat with her hands. She did not use silverware.
2. She would put the food in the mouth and would spit the food out.
3. If dessert served along with the entrée will eat the dessert first.
4. Excessive spillage of food.
5. Eats 95%-100% of her food.
6. If dessert not served immediately after she finishes her entrée, she will leave her dining table.
7. Helen likes to snack on fruits.
8. Helen does not like water, she prefers juice.
9. Helen is unable to use her napkins appropriately.
10. Helen loves coffee.
11. Helen only takes her medication in a chocolate pudding.

An example care plan developed for such a scenario for Helen is as follows:
1. Helen follows very simple clear directions. Talk to her slowly and clearly. Lean forward when talking to her. Talk to her with a smile and use a friendly tone. When it is time for meal time, tell her the following "Helen, its time for breakfast, why don't you join us. Would you like to sit down? I have your favorite cup of coffee"
2. After Helen sits down—Set her silverware and her napkins. Serve her decaf coffee immediately. Allow and encourage her to enjoy her coffee.
3. Cut her food into small pieces and encourage her gently to use her silverware.
4. Dessert must be served immediately after she eats her entrée.
5. Look for spillage on the floor around the table. Clean the floor after Helen finishes her meal.

Grooming: After observation, it was noticed that Helen likes to carry a comb in her pocket. She combed her hair throughout the day. This leads suggests that she is very conscious of how she looked. She was independent with grooming. Helen doesn't like make up. She likes to wash her face and dry it with a towel. She prefers to apply Johnson's baby lotion on her face and hands. She can do it on her own with slow, clear, simple step by step instructions. She also likes to use her perfume.

Care Plan: In the morning after Helen completes her activities of daily living, lead her to the bathroom or to a mirror by giving her simple instructions such as "Helen would you like to comb your hair? I think it's time to get ready and go out for breakfast."

Direct Helen to the Johnson's baby lotion in the medicine cabinet. Instruct her gently to reach forward to the cabinet and pick the bottle. The instruction should be in the following sequence—
1. Can you open the cap for me?
2. Could you squeeze the bottle and pour the lotion on your hand.
3. Now rub between both of your hands and gently apply them on your face.
4. Can you get around your nose, below your eyes, around your ears and down under your chin by your neck.
5. After she applies the lotion, hand her the perfume and have her spray under her ears.

Oral Hygiene: Helen is independent, able to brush her teeth with simple directions. Squeezing the tooth paste out of the tube can be difficult for Helen. She needs assistance with applying tooth paste on the brush. Sometimes, she puts the tooth brush in her mouth and stares into the mirror.

Care Plan: With gentle slow, clear instructions, direct Helen to the front of a sink. Have her stand in front of the mirror. Have her reach for the tooth paste and brush from her medicine cabinet. Apply the tooth paste on her brush within her line of vision so that Helen can see and watch this being done. Have small talks with Helen related to applying the tooth paste and the need for her to brush her teeth. The small talk should discuss the benefits of brushing her teeth and how it is nice to have clean beautiful teeth. Talk about how it would improve Helen's smile and how beautiful she would look. After applying the paste on her brush, ask Helen politely to put the brush in her mouth and begin to brush her teeth. Give her simple instructions such as brush the lower left side, slide the brush to the right and brush the right lower side. After brushing her teeth, have her rinse her mouth with water followed by her mouth wash.

Dressing: Helen likes to put on several layers of clothing. She has difficulty buttoning/unbuttoning her blouse. She sometimes put them backwards. Helen feels cold all the time. She has a favorite fleece jacket that she likes to wear all the time. Helen loves her turtle neck. Sometimes she has difficulty putting her pants on. She puts her right leg in her left and her left leg in her right sleeve. She likes to wear her pair of black shoes. She uses adult diapers. She needs help with overall dressing. Helen likes to get dressed by her bed in the bedroom.

Care Plan: The caregiver should pick Helen's clothes every morning. Lay the clothes on the bed and ask for Helen's approval. Make sure that her fleece jacket and black shoes are part of the arrangement. Since Helen likes turtle necks, make sure that she has a turtle neck blouse. Arrange her black shoes and socks for her to see. After getting an approval from Helen, the caregivers should follow the directions in the following sequence.
1. Lead Helen to her bedroom after her wash/bath routine.
2. Ask Helen to stand up straight and tall. Inform her when intending to put her diaper. Ask her to lift her leg up and slide it in the left hole of the Depends. Repeat the same with her right leg. Make sure that Helen is holding on while help pull her diaper up to her hip.
3. Assist Helen with her upper body dressing. Lean forward and give her slow clear instructions to gently slide her left hand into her left sleeve followed by her right. Pull the sleeves all the way up to her shoulders. Instruct her to slide her head and pull the blouse all the way down her upper body. Compliment her on the turtle neck and how beautiful Helen looks. Do the same with her lower body dressing. Tell her how great she looks and how enjoyable it is to work with her.
4. Show her the fleece jacket and emphasize that it is known how much Helen loves the fleece jacket. Compliment her again.
5. Assist her with her socks and shoes. If Helen can assist, ask Helen to help. Tell her it is good to help, and that the more she can help, the better it is for her.
6. Continue to compliment Helen and let her know that how enjoyable it is working with her.

Bathing: Helen needs extensive assistance with bathing. She is fearful of falling. Helen has fallen twice in her home.

Care plan: Make sure that the bathroom is clutter free. Set the soap lotion, shampoo, towel within reach of the caregiver. Make sure that there is a towel or a mat by the shower. Set the shower stool appropriately in the shower. Pull the shower head to maneuver it safely and functionally. All the supplies and everything requires must be within the caregiver's reach. Rehearse the whole bathing routine before bringing Helen into the bathroom.

1. Walk up to Helen and explain the entire bathing routine. Make sure Helen listens to your instructions. Inspire confidence as Helen is fearful of falling. Explain the entire process. Explain the plan to walk her to the bathroom, the plan to help her undress, the plan to make sure that the water is of the right temperature, the plan to help her with applying soap solution, the plan to shampoo her hair and the plan to dry her.
2. Ask Helen to stay close to help bathe her safely
3. Assure Helen that you are right by her and you wouldn't let her fall.
4. Inform the steps planned to take before the steps are initiated and completed. Keep Helen engaged and part of the entire process. If Helen can help with little steps, encourage her to do so.
5. Before leading Helen to the shower, run the water to get the desired temperature. Encourage Helen to feel the water to help her gain confidence and trust. Ask her if she thought that water was OK and at her desired comfortable temperature. After her approval initiate the bathing process.
6. Inform her that her whole body will be rinsed first.
7. Apply soap to her hands and her upper body.
8. Apply soap to her back.
9. Apply soap to her lower body and legs.
10. Apply soap to her private area.
11. Inform her that her whole body will be rinsed.
12. Apply shampoo gently to her hair in the head. Do not leave the shampoo for too long, rinse the hair quickly after shampoo application.
13. Inform Helen when turning the water off. Cover her with a large towel.
14. Dry her body from head to toe.
15. While drying her, continue to engage with Helen describing the next steps and actions such as "I'm going to wipe your back. I'm going to rub your back in a circular motion with the towel."

It is important to talk to Helen continuously to inspire and ensure confidence and trust. Confidence and trust enables an individual to participate and cooperate. There is a harmony. The individual enjoys the care and the caregiver enjoys the caring process. Caring for an individual is a partnership, a marriage between the caregiver and the individual. Each party should understand each other and be in terms with each other. It is the responsibility of the caregiver to initiate and develop trust, confidence and a very comfortable setting.

If an individual is wheel chair bound, the individual will require assistance with transfers from the wheel chair to bed, bed to wheel chair, wheel chair to toilet seat, toilet seat to wheel chair, wheel chair to recliner and recliner to wheel chair. Individuals in a wheel chair most commonly have fear of falling. It is important for the caregiver to develop the trust and confidence from the individual. Every step of the wheelchair must be clearly articulated to the client. Sometimes, the steps may have to be further broken down to mini-steps.

The care plan must be followed to detail as designed by the nurse. It is important that every caregiver follows the instructions. Such instructions could be provided using paper clipboards, or tablet computers that may be networked to a central server. There should be no deviation from the care plan. The care could be provided by different individuals, however, the steps to execute the care plan must be the same. There should be consistency with the execution process. If one caregiver deviates from the care plan, that caregiver is doing a disservice to the individual patient, and is negatively impacting an individual's care and well-being. If the same steps are followed and repeated every day, theoretically, the individual is subjected to the same stimulus again and again. The brain has the ability to retain, learn the ADL and cognitive functions. Learning happens because of repetition. Repetition done routinely could create structure. This will enable individuals with dementia/Alzheimer's retain substantial function. It may also pave way to learn higher skills and functions.

Activities:

There are a total of seven learning areas that the treatment program incorporates in an activity. They are Social-emotional skill, large motor skill, small motor skill, visual skill, reasoning skill, language skill and listening skill. These basic seven skills are required to learn, develop and retain the basic activities of daily living functions such as feeding, grooming, oral hygiene, dressing, bathing, toilet hygiene and ambulation. While an activity has one primary purpose, several skill areas are often touched when the activity is presented. For example, when an elderly individual plays a corn-hole game, the individual is not only perfecting a large motor skill that develops and strengthens balance and posture that one needs to dress the lower body, ambulation, grooming and oral hygiene but also the ability to share the bean bag (social-emotional skill), follow direction (listening), leaning down and forward to pick the bean bag with their hand using their fingers to grasp the bean bag (small motor skills), looking at the board and aiming at the hole (orientation, visual-spatial activity or depth perception).

Treatment Program Accomplishments:

The treatment program is therapeutic in nature. The objective and goal of the program is to enable individuals to retain their basic ability to function (Cognitive and activity of daily living) and consequently re-introduce the individuals to lost ADL functions and gradually progressing them to re learning newer activity of daily living skill.

A Dementia/Alzheimer disease diagnosis is established based on one's ability to perform basic activities of daily living and cognitive functions appropriate to their age. The severity and the stages of the disease are established based on one's ADL and cognitive abilities and disabilities.

The objective and the goal of the program is to enable individuals to function at their best ability and highest potential. The program treatment hypothesizes that having an individual live in an environment that is serene, tranquil calming and peaceful diminishes the unnecessary clutters such as anxiety, depression, memory conflicts and agitation. This enables an individual to be at peace and free of unnecessary emotions that potentially could be a hindrance and barrier for optimum brain function. Diminishing the unwanted emotions may also clear and align thoughts that potentially could help with recalling retained memory. Consistent and constant repetition of activities of daily living functions daily may trigger registration of those skills. Reinforced with activities that incorporate and foster basic learning areas also contribute to retention and possibly development of lost functions. All of these contribute to either retention of the existing function or development or lost function. Thus, the treatment program could slow the progression of the disease by prolonging the stages of the disease.

In particular, an example embodiment of the system and method are described in the following paragraphs:

Skyscape Lighting:

The ceilings of assisted living facilities can be adapted to simulate a natural sky using example SKY PANELS to form a "Skyscape". Examples of such lighting are shown in FIGS. 3A-3D, 4A-4B, and 5. Note the changes in lighting and coloring that show the transit of the day, particularly the difference between FIG. 4B and FIG. 5, with FIG. 4B providing lighting reminiscent of full daylight, whereas FIG. 5 reflects an evening, twilight lighting effect. Other periods of time can also be represented, such as morning and nighttime (which may be a dim moonlight effect, stars, or just an off setting of full darkness). Also note the appearance of clouds in the lighting of these figures. Other sky features could also be represented, such as the sun, stars, the moon, etc. The sky scape affect can be made possible, for example, by installing translucent acrylic panels that have images of the sky on them.

The dimensions of the example SKY PANELS are— 23¾%×47¾% and 2×4 sheet. The ceiling is broken down into multiple light zones to provide a controlled lighting affect. In this example, the zones use florescent bulbs and a Lutron ballast. The Lutron ballast is used to dim and brighten the bulbs using a software program executing on a computer to control the lighting affect. The lights are controlled (brightened and dimmed) by the software program according to a desired process, which may include a control system such as shown in FIG. 1 and described in more detail below for running a control program to simulate effects that reflect the actual transition of daylight. Note that other types of lighting and/or control systems could be utilized. For example, LED based lighting could be used instead of florescent lighting, as modern LED lighting is proving very versatile in its lighting effects.

In this example, the control program provides an effect mimicking the natural sunrise and sunset, and daylight. The bulbs from different zones are turned on gradually, becoming bright over time to create a day light effect to provide a daylight period of a desired length. The length of the "day" created by the Skyscape is based on the needs of the patient, and hence daylight may transition over any desired timeframe. For example, a day may be 6 hours, 8 hours, 12 hours, 16 hours, or something in between. When it is desired to show the day ending, such as around 2.00 PM, 4:00 pm, 6:00 pm, 9:00 pm, or any other desired time, the lights are controlled to begin to dim in a gradual manner (e.g., to enter twilight) and ultimately proceed to turn off to give an evening and a night effect. Of course, night lighting showing stars, etc. can also be simulated. The sky scape light can thus be controlled to provide the external sunrise and sunset, daytime, and nighttime routine and thereby mimic the affect of transition from day to night, to be repeated on a daily basis, all under control by the computer executing the software program. This gives the illusion of a normal day that the patient has experience over his or her lifetime.

The natural sky scape along with the day and night routine could be used to encourage and facilitate a routine for the patients that humans are accustomed to all their lives. The day and night routine influence and dictate human functions and well-being. Such a routine conveys a time to wake up, time to carry out basic activities of daily living functions, time to work, time to rest, time to eat, time to play, time to relax and time to sleep. A simulated sky scape takes an individual (patient) with, for example, Dementia/Alzheimer disease through the routines of morning, afternoon, evening, and night. This routine can enable and establish structure after consistent constant repetition. This can enable the individual with Dementia/Alzheimer disease to lead a life with a regular schedule including routine and structure. The individual may relearn to recognize the time to wake up, perform routine basic activities of daily living, follow meal times, play, relax and rest. This routine could facilitate the normal human biological clock thus promoting function and well-being.

Skyscape in this example is designed to effectively create functional illusions of the real sky (see FIGS. 3A-3D, 4A-4B, and 5). Sky image ceilings have the ability to produce a physiological relaxation response in observers, to change subjective experiences of space in interior environments, and to produce certain beneficial effects. Such images trigger the same psycho-physiological relaxation response as an experience of the real sky. The Skyscape can be used to modify individuals subjective experience of vertical space. Like an experience of real sky, Sky ceilings trigger a genuine response, a fundamental physiological and emotional style of functioning that leads to an expanded sense of space, comfort and inner stability. Cognition is a complex and incompletely understood process that includes mental activity shaped by millions of years of human evolution, along with the influences of humans. Conditioning, knowledge and memories acquired since birth. Cognition functions to create a true and useful picture of reality, providing:

Illusions are perceived as something other than what they are.

A simple way of understanding how we know things is:
A way to experience a thing or event through one, or more, of our senses.
A means of dealing with this raw information via the processes of cognition
Providing Cognition resulting in perception—thoughts and/or feelings that identify the experience and our response to it.

Deliberate illusions are generally intended to trick the eye and/or confuse the process of cognition. Cognition, an important aspect of the process of knowing, is based on the activity of a complex arrangement of habits which are established and maintained by previous experience and are expressions of the mind's fundamental neural pathways. Basically, habits of perception function as efficient generalized solutions to the interpretation and perception of the large amount of data provided by the senses. However, efficiency gained through generalization may be accomplished at the expense of accuracy—hence the misperceptions of illusion.

Sky image ceilings are crafted to create as convincing an illusion of sky as possible (FIGS. 3A-3D, 4A-4B, and 5). Skyscape triggers slowing of breathing rate, relaxation of musculature including spontaneous smiling, marked psychological relaxation, reduction in anxiety levels, increased sense of wellbeing and refreshed alertness. Captive observers of sky image ceilings experience these illusions largely through their frontal (central) vision and, considering their vision is directed only toward the ceiling; have little choice about where their visual attention is directed. In such cases, (assuming optimal size and placement) the sky image ceiling typically occupies the observer's entire field of frontal vision (and some portion of the peripheral vision as well) and the patterns of clouds and vegetation become visual elements, the exploration of which is the subject of the observer's attention. Where an observer may be seated or standing beneath a sky image ceiling, their attention, and consequently their frontal vision, is typically directed elsewhere, toward some other activity. In such a case the sky image ceiling is experienced primarily through peripheral vision. However, because peripheral vision serves as our security or safety system, it appears that the constant stimulation of sky overhead, communicates important information about the condition of our physical environment that in turn triggers further erroneous or misperceptions.

Peripheral vision of individuals is good at detecting motion (a feature of rod cells), and is relatively strong at night or in the dark, when the lack of color cues and lighting makes cone cells far less useful. The distinctions between central (frontal) and peripheral vision are reflected in subtle physiological and anatomical differences in the visual cortex. Different visual areas contribute to the processing of visual information coming from different parts of the visual field, and a complex of visual areas located along the banks of the inter hemispheric fissure (a deep groove that separates the two brain hemispheres) has been linked to peripheral vision. It has been suggested that these areas are important for fast reactions to visual stimuli in the periphery, and monitoring body position relative to gravity.

Skyscape, when used as described, helps to eliminate discomfort and claustrophobia. The experience is characteristic of ease and comfort of an outdoor space. Bright light—both natural and artificial—can improve health outcomes such as depression, agitation, sleep, circadian rest-activity rhythms, and persons with seasonal affective disorders (SAD). Bright light is effective in reducing depression among individuals with bipolar disorder or SAD. Exposure to morning light is more effective than exposure to evening light in reducing depression; that exposure to bright morning light has been shown to reduce agitation among elderly with dementia; that exposure to bright light improves sleep and circadian rhythms. Individuals exposed to an increased intensity of sunlight experienced less perceived stress, less pain, took less analgesic medication and had less pain medication costs.

Viewing nature or images of nature: has stress-reducing or restorative benefits such as positive emotional and physiological changes; that stressful or negative emotions such as fear or anger diminish while levels of pleasant feelings increase; that viewing nature produces stress recovery quickly evident in physiological changes, for instance, in blood pressure and heart activity; can serve as positive distractions for patients; can help reduce the use of pain medications.

Accordingly, by utilizing the Skyscape in the treatment and living quarters of patients by applying the disclosed method, the benefits identified above can be provided for these patients in their treatment, therapy, and daily living conditions.

The Relaxation Response

The relaxation response, the opposite of the fight or flight response, is triggered by a wide range of relaxation and meditative techniques including contemplative experiences of nature. It is characterized by the following physiological correlates:

Metabolic rate decreases;
Heart beats slower and muscles relax;
Breathing becomes slower;
Blood pressure decreases;
Levels of nitric oxide are increased; and
Brain wave patterns change in specific ways.

The relaxation response can be used as an antidote for stress and as an important element in maintaining stable health as well as creating conditions supportive of the healing process. Several physiological indicators of stress can be changed by the practice of meditation—proving to be an effective alleviator of the deleterious effects of stress. Even fairly brief encounters with real or simulated nature settings can elicit significant recovery from stress within three minutes to five minutes at most (Parsons & Hartig, 2000; Ulrich, 1999, incorporated by reference). Stress-reducing or restorative benefits of simply viewing nature are manifested as a constellation of positive emotional and physiological changes.

Stressful or negative emotions such as fear or anger diminish while levels of pleasant feelings increase. Laboratory and clinical studies have shown that viewing nature produces stress recovery quickly evident in physiological changes, for instance, in blood pressure and heart activity (Ulrich, 1991). Nature serves as a positive distraction (Ulrich, 1991) that reduces stress and diverts patients from focusing on their pain or distress.

Figure 6:
FIG. 6 is a photograph showing a simulated outdoor scene with functioning flowing water arrangements.

Flowing Water, Water Falls:

The breaking of the surface of water, by waves, falls, or evaporation, releases negative ions in the atmosphere. By their ability to stick to different free radicals, such negative ions are very beneficial to the health of individuals with dementia and Alzheimer disease. FIG. 6 shows an example waterfall both partially painted on a wall and including a flowing water arrangement to give the sight and sound of actually flowing water along with providing beneficial ions.

Both positive and negative ions occur naturally in the air. However, the environment we live in today has far more sources of positive ions, creating an electrical imbalance in the air and our bodies. They are also called free radicals. Free radicals are atoms, molecules, or ions with unpaired electrons, and thus tend to be highly reactive. They "steal" electrons from healthy cells to neutralize their own charge, causing cellular damage, therefore such free radicals are closely associated with oxidative damage and the degenerative aging process.

Positive ions can damage cells by changing the Acid-Alkaline balance in our body, and are believed to be the reason for the deterioration of our physical and emotional wellbeing heaving a role in the aging process and cancer. People that spend too much time indoors suffer from headaches, poor concentration, allergies, and depression. An astonishing small quantity of negative ions could kill bacteria and quickly take them out of the air so they were less likely to infect people.

Springs, waterfalls, sea waves, forests, and gardens contain high amounts of electrically charged particles (negative ions) in the atmosphere that ease tension while leaving us full of energy. Atmosphere charged with such negative particles offer a wealth of physical and psychological benefits.

Naturally Generated Negative Ions can have many health benefits, like: enhance the immune system, increase alertness, increase work productivity and concentration, reduce susceptibility to colds and flu, relief from sinus, migraine, headaches, allergies and hay fever, reduce the severity of asthma attacks, increase lung capacity, stabilize alpha rhythms (a pattern of smooth, regular electrical oscillations in the human brain. These normally occur when a person is awake and relaxed. The machine used to record these waves is called an electroencephalograph, or EEG. Alpha Rhythms have a frequency of 8 to 13 hertz. Also called alpha wave), cure depression syndrome.

Falling waters, water waves, or water evaporation from plants, create thousands of negative hydrogen ions by splitting water molecules. The negative electrons join with other free positive electrons in the air neutralizing their electrical charge. These negative ions appear to have an effect in changing mood. The sound of falling water and its proximity can help individuals relax.

Near strong surf or close to a waterfall up to 10,000 negative ions can be found. Atmosphere charged with negative ions offer a wealth of physical and psychological benefits, like reduction of asthma and allergy symptoms and relief of seasonal depression, fatigue and nervousness. They also help improve performance of voluntary movements, increase work capacity and sharpen mental function.

Negative ions are beneficial to human body in four major ways:

Strengthen the functions of autonomic nerves

Reinforces collagen (tissues that are resilient and tension-related)

Improves the permeability of the cell's prototype plasma membranes (improves metabolism)

Strengthens the body's immune system

Negative ions neutralize pollutants and provide positive effects on health to stimulate the reticulo-endothelial system, a group of defense cells in our bodies that marshal our resistance to disease, act on our capacity to absorb and utilize oxygen. Negative ions in the bloodstream accelerate the delivery of oxygen to our cells and tissues, speed up oxidation of serotonin (5-hydroxtryptamine) in the blood. This is well known to have far reaching effects on mood, pain relief and sexual drive.

It has been postulated that an energy system within our bodies consists of two forces, magnetism and electricity, with the electricity component consisting of low-frequency direct-current (DC) electric field. This electromagnetic energy system is affected by the earth's natural electromagnetic environment, which is normally relatively quiet, with minor rhythmic variations, but which experiences great increase in an electromagnetic charged environment. Thus:

The negative charged environment has stimulated the body's own healing mechanism in the case of stress and specific physical problems. Increase blood flow with resultant increased oxygen-carrying capacity, both of which are basic to help the body healing itself;

Changes in migration of calcium ions which can either bring calcium ions to heal a broken bone in half the usual time, or can help move calcium away from painful, arthritic joints;

The pH balance (acid/alkaline) of various body fluids. (Often out of balance in conjunction with illness or abnormal conditions)

Hormone production from the endocrine glands can be either increased or decreased by Negative Ion stimulation;

Altering of enzyme activity and other bio-chemical processes.

Studies have also shown a link between negative ion treatment and benefits for the following:

Migraine Headaches: Inhaling negative ions regulates the production of serotonin inside the brain. The overproduction of serotonin inside the brain is the cause of migraine headaches. Low Serotonin levels are believed to be the reason for many cases of mild to moderate depression which can lead to symptoms like anxiety, apathy, fear, feelings of worthlessness, insomnia and fatigue. Serotonin is thought to play an important role to our mood, thought processes, sleeping patterns, eating patterns, reaction to external stimuli and control of motor activity. People feel positive about both themselves and the world around them.

It was shown that the increase of serotonin levels in the blood can treat cases of mild to moderate depression which can lead to symptoms like anxiety, apathy, fear, feelings of worthlessness, insomnia and fatigue. Near strong surf or close to a waterfall up to 10,000 negative ions can be found. Atmosphere charged with negative ions offer a wealth of physical and psychological benefits, like reduction of asthma and allergy symptoms and relief of seasonal depression, fatigue and nervousness. They also help improve performance of voluntary movements, increase work capacity and sharpen mental function.

Depression: A study at Columbia University suggested that negative ion treatment is more effective than anti-depressant drugs such as Prozac and Zolof, and there are no side effects with negative ions.

Fatigue: The overproduction of serotonin (chemical produced inside the brain) also causes fatigue, and negative ions regulate the production of serotonin inside the brain.

Sleep: A study in France found that negative ionizers helped people to sleep better, by regulating the production of the chemical serotonin in the brain.

Mental Performance and Concentration: Several tests have shown people exposed to negative ion treatment perform much better in mentally-oriented activities than those who are not.

Physical Performance: Due to test results performed by Russian scientists, negative ionizers were always installed in the locker rooms and resting places for the Russian athletes.

Figure 2A:
FIGS. 2A-2B are color photographs showing an internal hallway connecting various patient rooms giving the impression of an outdoor entrance.
Figure 2B:
Figure 3A:
FIGS. 3A-3D are photographs showing public living arrangements according to one example embodiment using example disclosed treatment procedure and including various uses of Skyscape lighting.
Figure 3B:
Figure 3C:
Figure 3D:

Plants:

Medium to small size plants and shrubs are planted in the planters in the common area outside the homes to simulate a natural external environment. Biophilic spaces can reduce unnecessary stress and depression, enhance positive social response, speed up recovery times, provide clients with dementia/Alzheimer's disease distractions, make tight and claustrophobic spaces seem wide open. Viewing nature imagery reduces systolic blood pressure and pulse; helps redirect negative thought and decreases boredom. FIGS. 3A, 3B, 3D, 4A, 4B, 5, & 6 show examples of both real plants and painted nature scenes being provided indoors. Furthermore, rooms that are intended to give the impression of being outdoors may also include the use of artificial turf, such as shown in FIGS. 2B, 3B, and 3C among others. Thus, the illusion of being outdoors in a natural space is reinforced.

Natural spaces stimulate imaginations and creativity, and playing outdoors enhances cognitive flexibility, problem-solving ability, and self-discipline. Taking a "green walk" decreases depression, reduce tension and increased their self-esteem. Nature in forms as simple as a plant or trees help reduce stress, improve coping skills, and develop self-discipline.

In nature, people learn that challenge is actually the opportunity to improve oneself, develop an internal locus of control, and build confidence. Wilderness experiences give people an optimistic confidence in the predictability of nature and the pace of life, combined with a healthy ability to surrender control. Nature-goers learn to trust their innate ability to overcome both expected and unexpected obstacles and to appreciate that things work out even if they aren't in complete control. In short, they learn they can cope with whatever comes their way, which in turn builds confidence and a sense of self-efficacy and achievement.

Outdoor settings beg for activity rather than passivity. People understand and process environmental information through mapping, exploring, and interpreting the landscapes, obstacles, and surroundings. This type of physical activity reduces depression and anxiety, reduces the risk of disease, and improves psychological well-being. Spending time in nature's silence better acquaints individuals with dementia and Alzheimer disease with their own thoughts and feelings, leading to a sense of calm and inner peace. Direct contact with nature increases mental health and psychological and spiritual development. Benefits include stress reduction, a sense of coherence and belonging, improved self-confidence and self-discipline, and a broader sense of community. Exposure to nature areas increases positive emotions while negative emotions decrease only when exposure to natural areas is relatively high. Natural settings elicit a response that includes a component of the parasympathetic nervous system associated with the restoration of physical energy. Nature helps the brain to relieve 'excess' circulation (or activity) and to reduce the nervous system. Experience of nature can help strengthen the activities of the right hemisphere of the brain, and restore harmony to the functions of the brain as a whole.

Older adults who spend time outdoors may derive health benefits such as better sleeping patterns, less pain, decreased urinary incontinence and verbal agitation, better recovery from disability, and even increased longevity.

Age was inversely related to outdoor usage, so that older residents generally spent less time outdoors. People using assistive devices such as walkers or wheelchairs also spent less time outdoors. Elderly, who spent more time outdoors, were also more worried about falling outdoors; this might be due to being outside long enough to observe existing hazards and barriers. The disclosed program brings nature to the individuals door step. The individual with dementia and Alzheimer disease don't have to travel far from their home to access nature and to derive the benefits of nature.

Having access to nature and the outdoors is therapeutic for elderly with dementia and Alzheimer disease. Spending time outdoors may improve sleeping patterns, reduce pain, decrease urinary incontinence and verbal agitation, speed up recovery from disability, and even increase longevity.

Figure 4A:
FIGS. 4A-4B are photographs showing common gathering areas of additional public living arrangements according to one example embodiment using example disclosed treatment procedure and including various uses of Skyscape lighting.
Figure 4B:
Figure 5:
FIG. 5 is a photograph showing another example of Skyscape lighting in an evening mode.

Garden Like Setting:

The garden like setting includes a Gazebo, a pergola, suites built like homes and carpets that look like grass. These structures along with the plants and the sky ceiling emulate a natural garden like setting. A setting that gives them an impression that they are not locked within four walls. This set up provides elderly with Dementia/Alzheimer's a perception that they live in a natural setting that they as humans are accustomed to. This type of living to some extent may suppress the need for them to seek exit and minimize elopement. The need and the urge to go out could be reduced due to the fact that as they step out of their home, they may feel that they are stepping out to the outside world. FIGS. 4A and 6 shows an example of a garden-like outdoor setting.

Suites:

The design of living spaces such as homes and their color patterns have changed over time. The elderly with Dementia/Alzheimer's disease tend to retain their long term memory for a longer period of time. Their experiences and memories between the ages of early childhood to 21 years of age tend to be the last memories they lose. The loss of memory and life experiences is directly related to the stages of the disease that they are currently in. FIGS. 2A-2B, and 3A, for example, show entrances to examples of such suites.

As previously discussed, Alzheimer diseases have seven stages. One's cognitive function and activities of daily living function determines the stages of the disease. For example, the cognitive function and the activities of daily living function of an elderly patient at stage 7 of the disease is similar to the cognitive function and activities of daily living function of an infant. The cognitive function and the activities of daily living function of an elderly patient at stage 6 of the disease is similar to the cognitive function and activities of daily living function of a 12-18 months old. The cognitive function and the activities of daily living function of an elderly patient at stage 5 of the disease is similar to the cognitive function and activities of daily living function of a 18 months—3 year old. The cognitive function and the activities of daily living function of an elderly at stage 3 and stage 4 of the disease is similar to the cognitive function and activities of daily living function of a 4-10/12 year old. The cognitive function and the activities of daily living function of an elderly at stage 2 of the disease is similar to the cognitive function and activities of daily living function is similar to teenage to 20s. The cognitive function and the activities of daily living function of an elderly at stage 1 of the disease is similar to the cognitive function and activities of daily living function of 25+ year old.

According to theory of retro genesis, the brains are not fully developed until about 21 years of age. The human nervous system experiences myelination and the process of myelination are the strongest and the deepest until the age of 21. The process of myelination is weak after the age of 21. All the experiences that one encounters, all the learning that one acquires during the strong and deep myelination process tends to stay longer in the memory. All the experiences that one encounters, all the learning that one acquires during the weak myelination process (After the age of 21) tends to leave the memory first. Therefore, elderly with dementia/Alzheimer's disease tend to remember experiences, retain memories that they had acquired between the ages of 0-21 years of age longer.

Based on the above explanation, an eighty nine year old elderly with the Alzheimer disease between the stages of 0-7 could possibly have cognitive and activities of daily living function abilities of an infant to 21 years of age. They would remember their experiences of their youth between the years of 1924 through 1945 (around 70-80+ years ago).

Creating an environment or a memory capsule that the elderly are familiar with is a goal of the treatment. The rooms that they live in are decorated and designed to look like homes that were built in late 1920s. The interior design of the homes, wall color, floor color, floor texture, electrical fixtures, plumbing fixtures, and color patterns are similar to that time period. This allows the elderly to engage within an environment that they are familiar with, as their memory of that period is still intact. The patients become more comfortable and feel a sense of security, as opposed to living in traditional nursing home like rooms that are unfamiliar to them in style and decor.

Enabling individuals to live in an environment that they are familiar and comfortable with gives them a sense of belonging and ownership. They accept and welcome the living environment. They get the feeling that they live in their own home. The feeling of living in their own home makes them less anxious, less depressed, less agitated and less combative. These emotions, when prevalent, could impede access of information from their memory that is required to function safely, comfortably in one's environment. Providing an elderly patient with an environment free of potential triggers to emotions such as anxiety, depression would enhance their activities of daily living and cognitive function.

The elderly clients will be at peace and in terms with their surrounding environment when it is organized according to these principles. They are free of any unfamiliar stimulus that they potentially could perceive from an unfamiliar environment. The risk for elopement is minimized, the desire to seek exit is diminished. They thrive well within an environment that they are familiar with. They don't feel like they are in an institution.

Thus, the rooms are designed with a sky ceiling, showing the sun rising and sun setting along with darkness and showing the moon and stars in the night, giving the impression that they live outdoors, in an environment like any normal human. Providing lush landscaping with water falls gives them the impression that they live outdoors. Some of the elderly with the disease tend to seek exit or elope if they are housed in an institution-like setting. This customized environment gives them an impression that they are not locked in. It promotes freedom. It reminds them of a past that they still remember.

A complete through assessment is completed before an elderly client is admitted into the program. The following information is solicited from family and friends prior to admission and to determine eligibility—
1. The elderly's prior living set up and arrangement.
2. Pictures/photographs of his/her home including exterior and interior.
3. The interior décor and furniture arrangement within his/her living environment.
4. The stages of the Alzheimer disease is established.
5. The activities of daily living and cognitive abilities and the way the elderly client goes about executing and completing the activities of daily living function.
6. The life style of the elderly
7. The daily schedule and routine After the above information is obtained, the home is designed to the elderly's past living specifications based on their youth experiences.

Upon receiving the elderly client's daily schedule and routine, a care plan is established. The care plan entails the following components/tasks—Feeding, grooming, oral hygiene, upper body dressing, lower body dressing, upper body bathing, lower body bathing, ambulation, transfers from wheel chair to and fro toilet, transfers from wheel chair to and fro bed, transfers from wheel chair to and from chair/sofa/couch. Each task is further broken down to minute steps.

For example—Feeding: The program defines what the caregiver(s) supposed to say and how they say it to motivate a client to cooperate, participate and initiate feeding. Examples such as "it is time for breakfast and I have your favorite breakfast prepared, Breakfast is the most important meal of the day and we need to have breakfast to get a good start, Your daughter/son would like you to have a good breakfast etc. What the client prefers for breakfast and how they would like their breakfast arranged in front of them. What would they like to drink? Would they like to drink coffee or juice first? Should the drink be served along with the breakfast or should it be served after the client finishes their breakfast. How does the client like their napkins placed. Do they like it on their lap or on their chest. What are the instructions that are required to motivate the client to continue cooperate, participate and complete the feeding task. Write the instructions in details. Instructions can be such as a. Can you use your fork to pick the eggs, b. Put them in your mouth, c. Chew them gently and swallow, d. Take a sip of water, e. Can you reach with your right hand for the napkin and wipe your mouth, Remarks for care givers: The client tends to spill food around her plates and also on the floor. Clean the spillage as soon as the client is finished with her breakfast. Watch for hand mouth coordination. Watch for signs of tremors and if any are detected, inform the nurse immediately.

The steps are broken down to the minutest detail for the caregivers, nurses and the client. On a daily basis, if the caregiver ensures that the elderly client follows every step as instructed and directed by the care plan during every meals, the elderly client continues to practice the existing function every day. With daily repetition and practice, the elderly client will continue to retain the existing function. The probability or chance of losing the ability of the clients to feed themselves is minimized.

Similarly, a detailed care plan is designed for each activities of daily living tasks such as grooming, oral hygiene, dressing, bathing and functional transfers.

The key to success of this system depends on two elements—1) A thorough assessment of the elderly client to identify the abilities, disabilities, and functions. Design an elaborate and a step by step appropriate care plan based on the elderly client's basic ability to function; and 2) The caregiver must follow the care plan on a daily basis. The instructions and directions must be followed as indicated by the care plan.

Alzheimer/Dementia disease is diagnosed and staged based on having adequate cognitive function to perform their activities of daily living such as feeding, grooming, oral hygiene, dressing, bathing and functional transfers.

The suites are designed like regular homes. The photographic figures show examples of such designs. Homes that are arranged similar to those the clients with Dementia/Alzheimer's are accustomed to. The home structures incorporate brick, vinyl siding, shingles, gutters, porches and porch lights. The colors and designs are carefully chosen to emulate homes that were built in the early 1930s. The elderly with dementia/Alzheimer disease have some of their long term memories intact. This arrangement is designed to provide an impression that they live in a home rather than in a room. It takes away an institutional like setting and provides a supportive home like setting. Their long term memories include living in a home rather than a room. Therefore, this setting may allow them to live in their memories that they are familiar and comfortable with.

The suites use color patterns, designs, lighting fixtures, floor coverings, and moldings that were commonly used in the early 1930s. The goal is to leverage on their residual long term memory and to enable them to associate with settings that they are familiar with. Furnishing their home with items that they have lived with all along their life may give them the impression that they live in their own home rather than in a room or an institution. This could put them at ease and permit them to lead their life with less worries and stress. The individual with Dementia and Alzheimer's disease have residual memories. The memories are usually from their early life or as a result of a strong emotional experience. They live for the moment and the intent here is to keep them comfortable and in terms with their residual memories. The time capsule reminds them of their home setting and encourages them to be comfortable and at peace with what they remember and are familiar with.

A preferred layout is to make the outdoor look like a quiet suburban sub division. The rooms are made to look like the client homes from 1924-1945. There may be no common rooms except for a craft shop that looks like a street craft shop.

A daily routine is designed, such as getting up at Sunrise, completing activities of daily living, having breakfast, participating in activities, having lunch, participating in activities or entertainment, having dinner, going for a walk and going to bed. Rest and sleep is important for elderly with dementia/Alzheimer's disease. Inadequate sleep or rest causes exhaustion. It clouds the elderly's memory and impairs them, preventing function at their maximum potential. Inadequate sleep could cause restlessness, irritation, combativeness and agitation. If an elderly is lodged in an institution like setting, they wouldn't know the difference between day and night. It causes disorientation. Disorientation results in anxiety, combativeness, agitation and aggressiveness. All these unwanted emotions impact the elderly's memory and as a result the elderly's cognitive and activities of daily living function is compromised. The day and night lighting facilitates a scheduled normal routine that humans are accustomed to. It motivates and encourages the elderly to go about living their lives as they always did. It causes less disorientation, minimizes unwanted emotions such as anxiety, combativeness, agitation and aggressiveness. The routine helps them to lead a structured life. They know when it is time for bed. The nightly effect encourages them to stay in their rooms and more so in their bed. It facilitates rest and sleep. Below is a more detailed example of a daily activity plan:

Example Daily Activity Plan

Classify the elderly into groups based on the clinical stages of the Alzheimer disease and their developmental age. The clinical stages of the disease correspond to a certain developmental age. An activity design must incorporate the cognitive elements and functions that are appropriate to the development age. The activities must be chosen and designed based on the elderly's clinical stage of the disease and the developmental age. The developmental age groups are as follows:

Infant
12-18 months
18 months-3 year old
4-10/12 year old
Teenage to 20 year old An elderly with a developmental age of 12-18 months will not be able to do an activity designed for 18 months-3 yr. old. The activity must be developmental age specific for the elderly to participate, cooperate, tolerate and to initiate, process and complete an activity.

Daily activity breakdown:

A daily calendar may consist of a total of 16 activities with an execution time span of 20 minutes for each activity. Two activities should be presented and carried out in a 60 minute span. The daily activity schedule could be as follows-9.00 AM-9.20 AM, 9.30 AM-9.50 AM, 10.00 AM-10.20 AM, 10.30 AM-10.50 AM, 11.00 AM-11.20 AM, 11.30 AM-11.50 AM, 1.30 PM-1.50 PM, 2.00 PM-2.20 PM, 2.30 PM-2.50 PM, 3.00 PM-3.20 PM, 3.30 PM-3.50 PM, 4.00 PM-4.20 PM, 5.30 PM-5.50 PM, 6.00 PM-6.20 PM, 6.30 PM-7.20 PM, 7.30 PM-7.50 PM. The system activity PROGRAM will be carried out seven days a week.

Two of the activities should be of simple in nature where all the elderly from different developmental stages can participate, cooperate and tolerate together. An ideal activity will be of a simple activity where predominantly large motor skills dominate the learning aspect of the activity for e.g. Corn-hole, Golfing, balance activity etc. The above two simple activities must be completed in the following time frame-9.00 AM-9.20 AM and 3.30 PM-3.50 PM. Two of the activity slot should include one on one individual activity session. The activity personnel should feel free to alter activities to better suit the elderly's needs.

Ideally three activities should be presented and completed for each age group in a given day. The activity personnel must find a way to incorporate some elements of activity of daily living such as feeding, grooming, oral hygiene, dressing, bathing, ambulation, functional transfers in a designed activity, specific to the individual or the group's needs and their ability to function. Although, the activity is designed to use in groups of three to seven elderly, many of the exercises can be used with a larger group or the whole population.

While there is a primary purpose in each activity, several skilled areas are often touched on when the activity is presented. When an elderly is playing a cornhole game, they are not only perfecting a large motor skill but they are learning:

Talking with one another (social-emotional skills);
Follow directions (Listening);
Leaning down and forward to pick the bean bag with their hands (Large and small motor skills); and
Aim at the hole in the board, orientation to distance of the board, depth perception (Visual-spatial skill);

There are a total of 7 learning areas/skills that the example treatment program incorporates in an activity. They are as follows: 1) Social—emotional skill; 2) Large motor skill; 3) Small motor skills; 4) Visual-spatial skills; 5) Reasoning skills; 6) Language skills; and 7) Listening skills. It is best to limit all the activities to a 20 minute session.

Example Social-Emotional Activities
1. Magic Land—Act out a part from favorite TV show. Benefits—Memory, concentration, thought process, oral speaking skills; and
2. Play Dough—Benefits: Group participation, fine motor skills, social interaction.

Example Large Motor Activities:
1. Red Light, Green Light—Balance, spatial orientation, right/left discrimination;
2. Shot put—Upper body strengthening, balance, Gross motor coordination, eye-hand coordination;
3. Toss it throw it; and
4. Follow the yellow road.

Small Motor Activities:
1. Bumpy name tags—Memory, fine motor skills, eye hand coordination, concentration, attention span;
2. Penny pick-up—Counting skills, fine motor coordination;
3. Tracing a drawing—Attention span, concentration; and
4. Peg activity.

Example Visual Activities:
1. Real-people paper dolls—Orientation to self and body parts, right/left discrimination, memory, oral skills;
2. Mystery game—Identify simple objects and talk about them—shapes, sizes, characteristics etc.;
3. Body part puzzle—Identify body parts and assemble a life like doll;
4. Sand tracing;
5. Peg board designs;
6. Letter shapes;
7. Sand tracing;
8. Copy cat game;
9. Picture puzzle; and
10. Coin family portrait.

Example Reasoning Activities:
1. The opposite song; and
2. What is it made off—Naming composition of everyday objects, Benefits: Memory, thought processing.

Example Language Activities:
1. The whispering game—Repeat one to three syllable words as they are heard and passed from one to another in a group setting. Benefits: Memory, language, social interaction;
2. Picture talk;
3. Pick one and tell me why; and
4. Rhymes and finger plays.

Example Listening Activities:
What will happen next;
Now what; and
Pretending.

Assessment Process:

An initial functional assessment as described herein is completed by the nurse to determine the individual's activities of daily living and cognitive abilities. The individual is allocated to a group. Therapeutic activities that incorporate one or more seven building blocks are taught daily. The tasks are practiced daily for retention and application. Activities of daily living tasks that are desired to be learned and developed are introduced and practiced.

Daily assessments are completed by the lead for participation and performance.

Assessments are completed by the nurse quarterly to measure the functional outcomes—an individual's ability to initiate and complete the desired ADL task. If the quarterly assessment indicates that the individual is able to initiate and complete the desired ADL function, it will be concluded that the individual met his or her goal. If the quarterly assessment indicates that the individual is unable to initiate and complete the desired ADL function, the individual could be allocated to a different group, could be assigned a different lead or the individual could stay in the group and continue to work on the desired ADL function.

If the individual presents with the potential to learn other ADL skills, the individual could be assigned a different group or could stay in the same group. The nurse and the lead make a collaborative decision. The learning process begins with a new task as a new goal.

The severity of the Alzheimer disease is staged and established based on cognition, perception and activities of daily living function. The basic cognitive functions are alertness, ability to follow simple and complex directions, orientation, concentration, safety, problem solving, judgment, sequencing and thought processing. The activities of daily living functions are Feeding, grooming, oral hygiene, upper body dressing, lower body dressing, upper body bathing, lower body bathing, toileting, functional transfers (Ambulation with and without adaptive equipment's, wheel chair transfers) The seven learning areas are essential to learn, develop and continue maintain activities of daily living and cognitive function.

The described activity program hypothesizes that the seven learning areas are the basic foundation and the required precursors to develop, maintain and enhance an elderly's activities of daily living function. If the elderly is able to maintain some or all the elements of cognitive and activities of daily function by engaging in activities that incorporates the above seven learning with consistent repetition, he/she will be able to learn, develop and retain their activities of daily living functions. One's ability to perform one or more daily living function determines the severity and the stages of the disease.

A continuous consistent learning and application of the learning areas during their day to day activities could enable the elderly to perform at their highest potential. This will enable to complete their activities of daily living tasks at their maximum potential.

If the elderly patient is able to consistently participate in the activity program, there is a good possibility that the stages of the disease could be prolonged and hence slow the progression of the disease. The objective of the activity program is to provide the elderly a life filled with dignity, respect and love—A life that every human deserves.

Grouping

Large Groups: At the beginning of the day, the elderly clients should be brought together into one or several large groups (depending on the number of elderly clients, typically more than 6 individuals). In the large group, they are introduced to concepts that they will work on later in small groups or individually. The large group is also the natural setting for re-igniting listening skills (reading newspaper, current affairs etc.) and music, and for playing large motor games. In general, large-group activity should separate periods of small-group work and should come before introducing to new tasks. Large groups are for 7 or more adults.

Small groups: Small groups will be used to individualize guidance, directions and instructions. This group setting will encourage the individuals to come together and work on a specific task. A small group will consist of 6 or less adults.

Working in pairs: Many activities could be effectively used by two adults working together quietly-sharing the task and discussing it.

Independent work: A specific activity/assignment is delegated to work alone.

Free Play: Often, after the individual have had to focus on a particularly demanding activity or when they have mastered the work that the activity coordinator is helping others with, they should be engaged in an activity of their own choosing and liking. They should be encouraged to complete the task/activity independently. It is best to have not more than two small groups in independent or free play at one time. To do so is to invite disruptions. It is also important to limit the duration of these periods. Individuals with Dementia and Alzheimer disease have short attention spans.

The learning session could be between 30-45 minutes depending on the activity tolerance, attention span and the ADL task that the group members learn. The individuals are grouped based on three cognitive abilities—attention span to an activity, activity tolerance, ability to follow simple and complex directions and the ADL task that the individuals require to learn and develop. Each group is lead either by a caregiver, nurse or activity personnel. In a given day, there could be 5-7 groups. The activity personnel present a pre-selected activity that is appropriate to the group. The appropriateness of the activity is based on the ADL task that the group desires to learn and develop.

The group session, for example, can start at 9.00 AM and end at 7.00 PM with break times in between for meals, snacks and other individual personal needs. The group meets every day for five days in a row in a given week. The groups are subjected to different activities based on the seven building blocks to learn, develop and strengthen a required ADL task. On a given day, an individual could have up to 14 group sessions and be subjected to 7-14 therapeutic activities to build and strengthen one or two building blocks that are required to learn and perform an activities of daily living skill. The individuals in a group are assessed, and their participation and performance scored, on a daily basis (such information can be entered into a computer database for long-term monitoring, using such data entry points as a tablet, or computer terminal, for example). The score gives a snap shot of one's performance and progress within a group. It is not required or necessary for individuals to be on the same group every day and week. The individuals could be a part of the same or multiple groups on a given day or a given week. The categorizing of individuals in a group is strictly driven by their attention span and activity/task tolerance.

The goal of the lead is to provide opportunities for the individual to make positive memories in the group sessions, build a foundation for finding joy in learning and to claim each day as a chance to be the change in the individual's life. The primary goal of the lead is to make the individual feel smarter and generate a love for activities and learning. The activity/task is made fun and exciting by offering more time to explore, learn and grow in an engaging and a supportive environment. The learning is made fun by providing more time to complete projects, and more time for socialization with peers and the lead. Learning becomes fun when the individual fully cooperates and tolerates an activity/task. The individual's ability to complete a therapeutic task gives them a sense of accomplishment. This promotes self-respect and dignity.

The groups can be further classified based on one of the following learning techniques—Redshirting, looping, mixed and transitional, which are described below:

Redshirting: High performing individuals are grouped with low performing individuals. Holding and having the high performing individuals as part of low performing group enables the high performing individuals to feel a sense of accomplishment and to mature intellectually, socially and physically. This will give an opportunity for the individual to be class leaders, will get more attention from the lead and enable them to better handle the increasing demands of learning.

Looping: Looping occurs when the same lead spends time with one group for 12 months. Here, the individuals in the group remain the same every day and the same lead teaches them various ADL tasks. In this process the individuals and the lead in a group develop a deep relationship because of the longer time together. The lead understands the individual dynamics and the patient expectations, and the lead obtains a deeper understanding of individuals learning styles.

Transitional: A transitional group is designed to give individuals extra time they need to focus, learn and develop an activity/task. This group may consist of individuals with poor task tolerance and attention span. The individuals in this group are given extra time to adjust, understand and focus on a task. Here the individuals are encouraged to progress at their own pace. The curriculum, teaching practices should be appropriate for each and every individual's activity tolerance.

Mixed: This is another approach in meeting collective needs of the individual. The individuals in this group are diverse with their learning abilities and interests. This setting provides a mix of high and above average performers. The individuals in this group stay together for 6 months with the same lead. This will enable collaboration and friendships across all individuals, creating a unique community. It creates a sense of belonging and support leading to continuous progression of learning and development.

Interest Centers:

The treatment center (assisted living facility) can organize the space for activities depending of number of criteria—Activity/activities to be coordinated, the size of the groups, accessibility and use of materials, water source, electric outlet, the need for tables, the necessary light sources, access to snacks and drinks, access to restrooms, etc.

Figure 1A:
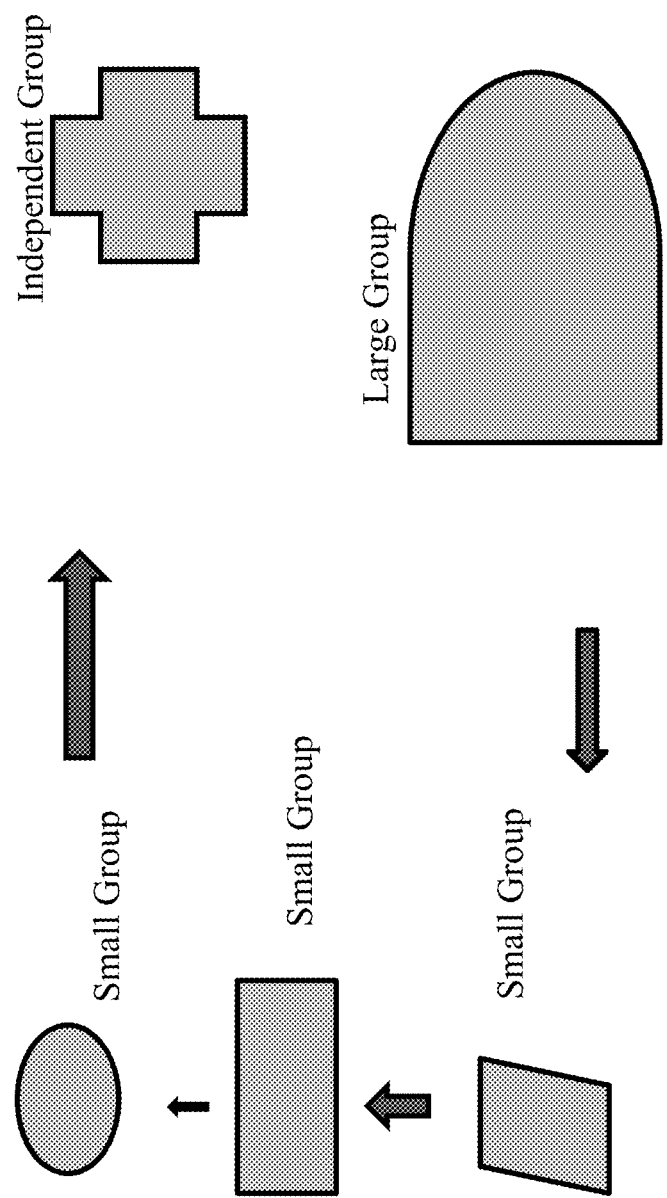

The activity centers that utilize some of the same materials should be provided close together. Activities involving focus and quietness should be held together and away from any type of distractions. Large groups require the most space. The activity with large materials may require storage space and hence should be close to areas that have storage space such as cabinets, shelves. A good activity center is one of the best ways to facilitate stimulation of the brain function. This will maximize free play, interaction and independent work. FIG. 1A shows one example of such an arrangement.

FIG. 1A shows a typical organization for an example activity center. The seating diagrams to the left are for one or more small group activities. The seating diagrams to the far right bottom are for a large group setting. The seating area in the upper right (shaped as a "plus sign") is for independent work. This layout is ideal to allow traffic to move ideally away from the large group. Once the clients engage in a large-group activity, they can scatter in various directions to small groups, free play and independent work.

Ideally, using the various groupings, or individually, three activities must be presented and completed for each age group in a given day. The activity personnel must find a way to incorporate some elements of activity of daily living such as feeding, grooming, oral hygiene, dressing, bathing, ambulation, functional transfers in a designed activity, specific to the individual or the group's needs and their ability to function. Although, the activity is designed to use in groups of three to seven elderly, many of the exercises can be used with a larger group or the whole population. While there is a primary purpose in each activity, several skilled areas are often touched on when the activity is presented. When an elderly is playing a corn hole game, they are not only perfecting a large motor skill but they are learning:

Talking with one another (social-emotional skills);
Follow directions (Listening);
Leaning down and forward to pick the bean bag with their hands (Large and small motor skills); and
Aim at the hole in the board, orientation to distance of the board, depth perception (Visual-spatial skill).

There are a total of 7 learning areas/skills that the treatment program incorporates in an activity. They are as follows:

Social—emotional skill;
Large motor skill;
Small motor skills;
Visual-spatial skills;
Reasoning skills;
Language skills; and
Listening skills.

The severity of the Alzheimer disease is staged and established based on cognition, perception and activities of daily living function. The basic cognitive functions are alertness, ability to follow simple and complex directions, orientation, concentration, safety, problem solving, judgment, sequencing and thought processing. The activities of daily living functions are Feeding, grooming, oral hygiene, upper body dressing, lower body dressing, upper body bathing, lower body bathing, toileting, functional transfers (Ambulation with and without adaptive equipment's, wheel chair transfers) The seven learning areas are essential to learn, develop and continue maintain activities of daily living and cognitive function.

The proposed activity program hypothesizes that the seven learning areas are the basic foundation and the required precursors to develop, maintain and enhance an elderly's activities of daily living function. If the elderly is able to maintain some or all the elements of cognitive and activities of daily function by engaging in activities that incorporates the above seven learning with consistent repetition, he/she will be able to learn, develop and retain their activities of daily living functions. One's ability to perform one or more daily living function determines the severity and the stages of the disease.

A continuous consistent learning and application of the learning areas during their day to day activities could enable the elderly to perform at their highest potential. This will enable to complete their activities of daily living tasks at their maximum potential.

If the elderly is able to consistently participate in the Aqua Lily's activity program, there is a good possibility that the stages of the disease could be prolonged and hence slow the progression of the disease. The objective of the Aqua Lily activity program is to provide the elderly a life filled with dignity, respect and love—A life that every human deserves.

Example Automation

Various features of the system and described methodology can be computer controlled to automate the process. FIG. 1 shows an example of such a system. The computer system includes a server 1, which can be provided in a locked maintenance room, executing a lighting program stored in a memory 2 for controlling lighting systems 5, 7, such as for implementing the Skyscape lighting process described above. Additional systems, such as a water system 9 for implementing flowing water such as waterfalls may also be controlled by the system. Output devices such as a printer 8 may be provided to allow for printing out reports, timelines, status information, etc. The computer system has at least one user interface 3 for receiving user inputs, such as scheduling information and lighting programming setup, and displaying information to the user, such as status information. This system can have components connected to the server via a network 6 or analog connections may be used for some components. A computer system of the type that can be used to turn outdoor lights on and off in other commercial applications can be adapted to control the lighting and other aspects of the system. For example, the computer program stored in the memory 2 can be designed to follow the Sunrise and Sunset established by the National oceanic and weather administration. The lighting systems 5, 7 can be for an entire building, or for each patient room individually controlled, for example, so that each patient my operate on a unique timetable.

Further automation can be provided by providing the various caregivers with communication devices, such as computer tablets, PDAs, computer terminals, or cell phones to act as user interfaces to allow for both data entry (such as the assessments and updates from observing the patients), and to display instructions, questionnaires, rules, schedules, etc. for aid in performing their jobs in caring for the patients. These devices can utilize their default operating systems and have customized programs to perform the customized functions, which may be accomplished using commercially available browsers running scripts obtained from central server, for example.

As will be appreciated by one of skill in the art, the example embodiments for automating the disclosed process may be actualized as, or may generally utilize, a method, system, computer program product, or a combination of the foregoing. Accordingly, any of the embodiments may take a form using a computer program stored on a computer-usable storage medium having computer-usable program code embodied in the medium for execution on a computer or computer system.

Any suitable computer usable (computer readable) medium may be utilized for storing the software. The computer usable or computer readable medium may be, for example but not limited to, an electronic, magnetic, optical, electromagnetic, infrared, or semiconductor system, apparatus, device, or propagation medium. More specific examples (a non-exhaustive list) of the computer readable medium would include the following: an electrical connection having one or more wires; a tangible medium such as a portable computer diskette, a hard disk, a random access memory (RAM), a read-only memory (ROM), an erasable programmable read-only memory (EPROM or Flash memory), a compact disc read-only memory (CDROM), or other tangible optical or magnetic storage device; or transmission media such as those supporting the Internet or an intranet. Note that the computer usable or computer readable medium could even include another medium from which the program can be electronically captured, via, for instance, optical or magnetic scanning for example, then compiled, interpreted, or otherwise processed in a suitable manner, if necessary, and then stored in a computer memory of any acceptable type.

In the context of this document, a computer usable or computer readable medium may be any medium that can contain, store, communicate, propagate, or transport the program for use by, or in connection with, the instruction execution system, platform, apparatus, or device, which can include any suitable computer (or computer system) including one or more programmable or dedicated processor/controller(s). The computer usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, radio frequency (RF) or other means.

Computer program code for carrying out operations of the example embodiments may be written by conventional means using any computer language, including but not limited to, an interpreted or event driven language such as BASIC, Lisp, VBA, or VBScript, or a GUI embodiment such as visual basic, a compiled programming language such as FORTRAN, COBOL, or Pascal, an object oriented, scripted or unscripted programming language such as Java, JavaScript, Perl, Smalltalk, C++, Object Pascal, or the like, artificial intelligence languages such as Prolog, a real-time embedded language such as Ada, or even more direct or simplified programming using ladder logic, an Assembler language, or directly programming using an appropriate machine language.

The computer program instructions may be stored or otherwise loaded in the computer-readable memory that can direct a computing device or system, or other programmable data processing apparatus, to function in a particular manner, such that the instructions stored in the computer readable memory produce an article of manufacture including instruction means which implement the function/act specified in the flowchart and/or block diagram block or blocks.

The software comprises computer program instructions that are executed by being provided to an executing device or component, which can include a processor of a general purpose computer, a special purpose computer or controller, or other programmable data processing apparatus or component, such that the instructions of the computer program, when executed, create means for implementing the functions/acts specified in the flowchart and/or block diagram block or blocks. Hence, the computer program instructions are used to cause a series of operations to be performed on the executing device or component, or other programmable apparatus to produce a computer implemented process such that the instructions which execute on the computer or other programmable apparatus the steps for implementing the functions/acts specified in this disclosure. These steps or acts may be combined with operator or human implemented steps or acts and steps or acts provided by other components or apparatuses in order to carry out any number of example embodiments.

Nurse's Station:

The nurse's station can be strategically located on one end of the facility to give a bird's view to the nurse's and caregivers of all the activities and events that occurs in the common area. The station is designed and located strategically that all client activity is easily visible and noticeable.

Example Principles:

The disclosed methodology is an exclusive function relevant program based on the theories of perception in action, retro genesis, progressive lowered stress threshold, person environment occupation (PEO) and basic ability to function (BATF). The objective of this methodology is to enable client patients to function to their best ability.

Example Goals and Objectives:

Prolong the time frame of the stages of the Alzheimer disease and consequently slow the progression of the disease.

Examples of how the Goals and Objectives are Accomplished

The severity of the Alzheimer disease is staged based on one's ability and inability to perform different elements of activities of daily living and cognitive function. The five principles in conjunction with the environment may enable the individual to perform their activities of daily living to their maximum ability and function. The more functional an individual is with their activities of daily living and cognitive performance, less severe is the disease.

The severity of the Alzheimer disease is staged and established based on cognition, perception and activities of daily living function. The basic cognitive functions are alertness, ability to follow simple and complex directions, orientation, concentration, safety, problem solving, judgment, sequencing and thought processing. The activities of daily living functions are Feeding, grooming, oral hygiene, upper body dressing, lower body dressing, upper body bathing, lower body bathing, toileting, functional transfers (Ambulation with and without adaptive equipment's, wheel chair transfers) The seven learning areas are essential to learn, develop and continue maintain activities of daily living and cognitive function.

Example Activity Program:

Hypothesizes that the seven learning areas are the basic foundation and the required precursors to develop, maintain and enhance an elderly's activities of daily living function. If the elderly is able to maintain some or all the elements of cognitive and activities of daily function by engaging in activities that incorporates the above seven learning with consistent repetition, he/she will be able to learn, develop and retain their activities of daily living functions. One's ability to perform one or more daily living function determines the severity and the stages of the disease.

A continuous consistent learning and application of the learning areas during their day to day activities could enable the elderly to perform at their highest potential. This will enable to complete their activities of daily living tasks at their maximum potential.

If the elderly is able to consistently participate in the Aqua Lily's activity program, there is a good possibility that the stages of the disease could be prolonged and hence slow the progression of the disease. The objective of the Aqua Lily activity program is to provide the elderly a life filled with dignity, respect and love—A life that every human deserves.

Appendix A, attached hereto and incorporated by reference, includes an example function centric care plan for an example patient. Appendix B, attached hereto and incorporated by reference, provides example functional assessment questions.

Many other example embodiments can be provided through various combinations of the above described features. Although the embodiments described hereinabove use specific examples and alternatives, it will be understood by those skilled in the art that various additional alternatives may be used and equivalents may be substituted for elements and/or steps described herein, without necessarily deviating from the intended scope of the application. Modifications may be necessary to adapt the embodiments to a particular situation or to particular needs without departing from the intended scope of the application. It is intended that the application not be limited to the particular example implementations and example embodiments described herein, but that the claims be given their broadest reasonable interpretation to cover all novel and non-obvious embodiments, literal or equivalent, disclosed or not, covered thereby.

What is claimed is:

1. A method of treating a patient with dementia, comprising the steps of:
   performing a functional assessment of the patient to determine the patient's cognitive and daily living capabilities;
   preparing, using said functional assessment of the patient, a customized cognitive and daily living capabilities plan including activities that the patient can execute:
   rehearsing individually with the patient the customized cognitive and daily living capabilities plan of the patient; and
   providing one or more rooms providing living quarters for the patient that are styled and organized according to memories of the past of the patient's life; and
   updating the customized cognitive and daily living capabilities plan to address progress of the patient as the patient progresses through the treatment.

2. The method of claim 1, further comprising the step of providing a lighting system in at least one room, said lighting system being configured to be controlled by a computer control system executing a lighting program for generating light from the lighting system adapted to simulate a plurality of different phases of daylight over a period of time.

3. The method of claim 2, wherein said period of time is between 6 and 24 hours.

4. The method of claim 2, wherein said plurality of different phases of daylight include morning, daytime, evening, and nighttime.

5. The method of claim 2, wherein said plurality of different phases of daylight include at least one period of twilight.

6. The method of claim 2, wherein said lighting system includes a structure adapted for simulating clouds.

7. The method of claim 2, wherein the step of providing at least one room comprising said lighting system further includes an apparatus for providing running water arranged in a manner to emulate a nature scene.

8. The method of claim 2, wherein the step of providing at least one room comprising said lighting system further includes providing live plants and paintings providing an illusion of the room being outdoors.

9. The method of claim 1, wherein the step of rehearsing individually with the patient the customized cognitive and daily living capabilities plan of the patient is rehearsed daily.

10. The method of claim 1, wherein said customized cognitive and daily living capabilities plan includes planning for dressing the patient and for personal grooming of the patient, such that the patient performs as many functions of the plan as the functional assessment of the patient has determined are possible.

11. The method of claim 10, wherein said customized cognitive and daily living capabilities plan includes generating written instructions for a caregiver to follow.

12. The method of claim 10, wherein said assessment determines an assessment of a plurality of learning areas of the patient including: social-emotional skill, large motor skill, small motor skill, visual skill, reasoning skill, language skill and listening skill for use in implementing the customized cognitive and daily living capabilities plan.

13. The method of claim 1, wherein said plan is updated to include new learned activities of the patient as the patient progresses through the treatment.

14. The method of claim 1, wherein said assessment determines an assessment of a plurality of learning areas of the patient including: social-emotional skill, large motor skill, small motor skill, visual skill, reasoning skill, language skill and listening skill.

15. The method of claim 1, wherein said functional assessment is performed over a period of days.

16. The method of claim 1, wherein the one or more rooms providing living quarters for the patient are styled and organized based on actual features used during the patient's youth.

17. A method of treating a plurality of patients with dementia, comprising the steps of:
performing a functional assessment of each one of the patients to determine each respective patient's cognitive and daily living capabilities;
preparing, for each one of the patients using said functional assessment of each one of the patients, a customized cognitive and daily living capabilities plan that each patient can execute;
rehearsing individually with each one of the patients, on a daily basis, the customized cognitive and daily living capabilities plan for that respective patient;
for each one of the patients, providing at least one customized room providing living quarters such that the customized room is styled and organized in a manner to remind the respective patients of living styles that were utilized during that respective patient's youth; and
updating the customized cognitive and daily living capabilities plan to address progress of each one of the patients as the respective patient progresses through the treatment.

18. The method of claim 17, wherein said functional assessments are performed for each one of the patients over a period of days.

19. The method of claim 17, wherein said customized cognitive and daily living capabilities plan includes a plan for dressing each patient and for personal grooming of each patient, such that each respective patient performs as many functions of the plan as the functional assessment of each respective patient has determined are possible.

20. The method of claim 17, wherein said assessment determines an assessment of a plurality of learning areas of each patient including: social-emotional skill, large motor skill, small motor skill, visual skill, reasoning skill, language skill and listening skill for use in implementing the plan.

21. The method of claim 17, wherein said plan is updated to include new learned activities of each patient as each patient progresses through the treatment.

22. The method of claim 17, further comprising the step of providing a lighting system in at least one common room, said lighting system being configured to be controlled by a computer control system executing a lighting program for generating light from the lighting system adapted to simulate a plurality of different phases of daylight over a period of time to simulate passage of a day.

23. A method of treating a patient with dementia, comprising the steps of:
performing a functional assessment of the patient to determine the patient's cognitive and daily living capabilities, said functional assessment including an assessment of a plurality of learning areas of the patient including: social-emotional skill, motor skill, visual skill, reasoning skill, language skill and listening skill;
preparing, using said functional assessment of the patient, a customized cognitive and daily living capabilities plan including a plan for dressing the patient and for personal grooming of the patient, such that the patient performs as many functions of the plan for dressing the patient and for personal grooming of the patient as the functional assessment of the patient has determined are possible;
rehearsing individually with the patient the customized cognitive and daily living capabilities plan of the patient; and
providing one or more rooms providing living quarters for the patient that are styled and organized according to the customized cognitive and daily living capabilities plan of the patient; and
updating the customized cognitive and daily living capabilities plan to address progress of the patient including adding new learned activities of the patient as the patient progresses through the treatment.

24. The method of claim 23, further comprising the step of providing a lighting system in at least one common room, said lighting system being configured to be controlled by a computer control system executing a lighting program for generating light from the lighting system adapted to simulate a plurality of different phases of daylight over a period of time to simulate passage of a day.

* * * * *